(12) United States Patent
Suh et al.

(10) Patent No.: US 8,785,518 B2
(45) Date of Patent: Jul. 22, 2014

(54) CURABLE ZIRCONIA ADHESIVE COMPOSITIONS FOR DENTAL RESTORATIONS

(76) Inventors: Byoung I. Suh, Oak Brook, IL (US); Liang Chen, Schaumburg, IL (US)

( * ) Notice: Subject to any disclaimer, the term of this patent is extended or adjusted under 35 U.S.C. 154(b) by 561 days.

(21) Appl. No.: 12/412,937

(22) Filed: Mar. 27, 2009

(65) Prior Publication Data

US 2010/0247738 A1 Sep. 30, 2010

(51) Int. Cl.

| | |
|---|---|
| *A61L 24/06* | (2006.01) |
| *A61K 6/083* | (2006.01) |
| *A61L 24/04* | (2006.01) |
| *A61K 6/08* | (2006.01) |
| *C08F 2/48* | (2006.01) |
| *A61K 6/00* | (2006.01) |
| *C09J 4/00* | (2006.01) |
| *C08F 230/02* | (2006.01) |
| *C08F 222/10* | (2006.01) |

(52) U.S. Cl.
CPC ......... *C08F 2/48* (2013.01); *C08F 230/02* (2013.01); *A61K 6/0023* (2013.01); *C09J 4/00* (2013.01); *C08F 222/1006* (2013.01)
USPC ......... 523/115; 523/113; 523/118; 433/228.1

(58) Field of Classification Search
USPC .................. 523/115, 113, 118; 433/228.1
See application file for complete search history.

(56) References Cited

U.S. PATENT DOCUMENTS

| | | | |
|---|---|---|---|
| 6,147,137 A | 11/2000 | Jia | |
| 6,512,068 B1 | 1/2003 | Nakatsuka | |
| 6,730,715 B2 | 5/2004 | Jia | |
| 6,750,268 B2 | 6/2004 | Hino | |
| 2004/0254261 A1* | 12/2004 | Kojima et al. | 523/118 |
| 2005/0154081 A1* | 7/2005 | Yin et al. | 523/115 |
| 2005/0175966 A1* | 8/2005 | Falsafi et al. | 433/215 |
| 2005/0252414 A1* | 11/2005 | Craig et al. | 106/35 |
| 2008/0293846 A1 | 11/2008 | Craig et al. | |
| 2009/0115084 A1* | 5/2009 | Moon | 264/16 |

FOREIGN PATENT DOCUMENTS

WO WO 2007079166 A1 * 7/2007

* cited by examiner

*Primary Examiner* — Michael Pepitone
(74) *Attorney, Agent, or Firm* — Ice Miller LLP

(57) ABSTRACT

The present application relates to a polymerizable dental adhesive system formulated for effective and durable bonding of zirconia based materials and restorations to dental resins and dental surfaces. According to one embodiment, a polymerizable dental adhesive system comprises a first acidic monomer comprising an ethylenically unsaturated polymerizable group or moiety of the general formula $CH_2=C_X-C(O)-$ wherein X is hydrogen, methyl or a lower alkyl group, and the first polymerizable monomer further comprises a phosphoric or phosphonic acid group of general formula $-OP(O)(OH)_2$, $-OP(O)(OH)$, $-C-P(O)(OH)_2$ and $-C-P(O)(OH)$, and a second polymerizable acidic monomer comprises an ethylenically unsaturated polymerizable group or moiety of the general formula $CH_2=C_X-C(O)-$ wherein X is hydrogen, methyl or a lower alkyl group, and wherein the second polymerizable acidic monomer further comprises a carboxylic acid group of the general formula $-C(O)OH$.

25 Claims, No Drawings

CURABLE ZIRCONIA ADHESIVE COMPOSITIONS FOR DENTAL RESTORATIONS

BACKGROUND

Aesthetic and biocompatibility considerations have greatly increased the demand for metal-free dental restorations in clinical dentistry, leading to great demand to replace the once-common metal or metal-backed ceramic fillings, crowns, veneers, bridges, posts, and other dental prosthetics and restorations with ceramic (also known as full-porcelain) versions of those restorations. However, traditional glass-ceramic and aluminum oxide ceramic restorations display a brittleness, high propensity for crack propagation, low tensile strength, and poor wear resistance that limits their use or longevity in many applications for dental restorations.

Zirconia-based technologies, such as zirconium-oxide materials, have greatly overcome the poor performance properties of traditional ceramic restorations with their high strength and comparatively higher fracture toughness, and may be used in endodontic posts, implants, and implant abutments, orthodontic brackets, cores for crowns, and fixed partial denture prosthesis frameworks, and other dental restorations. Further, zirconia provides the metal-free, aesthetic characteristics requested by patients, and its hard and dense surface is ideal for resisting wear damage making zirconia an attractive material for single tooth dental restorations.

However, while zirconia dental restoration materials (including those sold under the LAVA, CERCON, and PROCERA trademarks) show a marked improvement in wear and strength properties in dental applications over traditional ceramics, these materials have proven to be challenging to adhere to dentin (whether etched or unetched), enamel, resins, and other materials using traditional dental materials and techniques. The questions of how to prepare the internal surfaces of restorations and restoration cites, as well as what proper adhesive protocols will result in clinically optimal results are current challenges of zirconia bonding because the clinically established protocol of etching (i.e., with hydrogen fluoride) and silanation, effective for other glass ceramic materials, does not yield sufficient strength when applied in zirconia bonding. Thus the acid-resistant, silica free surface of zirconia creates difficulty in establishing a strong and stable bond between the zirconia internal surface and tooth structure.

Previous attempts to improve the adhesion between resin materials and zirconia include U.S. Pat. No. 6,939,901 to Nakatsuka et al. This system utilizes a two-part adhesive system comprising a first polymerizable monomer containing an acidic group and a second polymerizable monomer having a general formula of

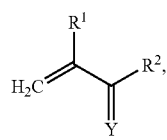

with $R^1$ being hydrogen or a methyl group; $R^2$ being a halogen; hydroxyl group, mercapto group, or —O—$R^3$—OH group; $R^3$ being an alkene group having 6 to 25 carbons; and Y being oxygen or sulfur. Similarly, U.S. Pat. No. 6,512,068 to Nakatsuka utilizes an adhesive system comprising a water-insoluble acid monomer having an alkene group of 8-25 carbons atoms, an alkyl group having 8-25 carbon atoms, an aromatic group, and an acid group selected from phosphoric acid, thiophosphoric acid, carboxylic acid, sulfonic acid, or another similar acid group, and a polymerizable unsaturated group selected from an acryloyl group, a methacryloyl group, a vinyl group, a styrene group; wherein the water-insoluble acid is present as a salt by combining the water-insoluble acid with a base in water to create a composition with a pH of 1.0 to 6.0. However, tests of commercial embodiments of these systems reveal bonding strengths between zirconia materials and other dental materials that would preferably be higher in clinical applications. Therefore an improved system for bonding, including greater bond strength and durability of bond between both resin materials and zirconia, as well as bonding between etched and un-etched dentin and resin materials in clinical applications would be appreciated in the art.

SUMMARY

The present application includes a dental adhesive system operable to bond materials to zirconia based materials, the system comprising a first acidic monomer having an ethylenically unsaturated polymerizable group of the general formula $CH_2$=CX—C(O)—R wherein X is hydrogen, methyl or a lower alkyl group, and wherein R comprises a phosphoric acid group or phosphonic acid group; a second acidic monomer having an ethylenically unsaturated polymerizable group of the general formula $CH_2$=CX—C(O)—$R_1$ wherein X is hydrogen, methyl or a lower alkyl group, and wherein $R_1$ comprises a carboxylic acid group; wherein the first acidic monomer comprises about 0.6% to about 10% of the dental adhesive system by weight; and wherein the second acidic monomer comprises about 2% to about 20% of the dental adhesive system by weight.

According to at least one embodiment, the abovementioned system optionally utilizes the first acidic monomer selected from the group consisting of $CH_2$=C(CH3)COO$(CH_2)_n$OP(O)(OH)$_2$ and $CH_2$=C(CH3)COO$(CH_2)_n$P(O)(OH)$_2$, wherein n is an integer from 2 to 20.

According to at least one embodiment, the abovementioned system optionally utilizes the second acidic monomer selected from the group consisting of tetrahydrofurfuryl cyclohexene dimethacrylate; the reaction product of 3,3'4,4'-diphenylsulfone tetracarboxylic dianhydride and 2-hydroxyethyl methacrylate; or biphenyl dimethacrylate. Further optionally, the dental adhesive system comprises at least one comonomer selected from the group consisting of 2-hydroxyethyl methacrylate, bisphenol A diglycidyl methacrylate, triethylene glycol dimethacrylate, 1,6-hexanediol dimethacrylate, ethoxylated bisphenol A diglycidyl methacrylate, and urethane dimethacrylate. Further optionally, the dental adhesive system of claim comprises an initiator.

In at least one optional embodiment, the dental adhesive system utilizes an initiator comprising at least one photosensitive ketone and at least one tertiary amine. Further optionally, neither of the acidic monomers of the dental adhesive system contain a halogen group.

According to at least one embodiment, the dental adhesive system comprises a ratio of the first acidic monomer to the second acidic monomer is between about 1:10 and about 3:1, respectively. Further optionally, the dental adhesive system comprises a ratio of the first acidic monomer to the second acidic monomer is between about 1:4 and about 2:1, respectively. Further optionally, the dental adhesive system comprises a ratio of the first acidic monomer to the second acidic monomer is between about 1:3.5 and about 1:1, respectively.

Other embodiments disclosed herein relate to a dental adhesive system comprising a first acidic monomer having an ethylenically unsaturated polymerizable group of the general formula $CH_2=CX-C(O)-R$ wherein X is hydrogen, methyl or a lower alkyl group, and wherein R is a phosphoric acid group or phosphonic acid group; a second acidic monomer having an ethylenically unsaturated polymerizable group of the general formula $CH_2=C_X-C(O)-R_1$ wherein X is hydrogen, methyl or a lower alkyl group, and wherein $R_1$ comprises a carboxylic acid group; at least one comonomer selected from the group consisting of 2-hydroxyethyl methacrylate, bisphenol A diglycidyl methacrylate, triethylene glycol dimethacrylate, 1,6-hexanediol dimethacrylate, ethoxylated bisphenol A diglycidyl methacrylate, and urethane dimethacrylate; an initiator comprising at least one photosensitive ketone and at least one tertiary amine; and a ratio of the first acidic monomer to the second acidic monomer selected from a range between: about 1:10 and about 3:1, respectively; about 1:4 and about 2:1, respectively; and about 1:3.5 and about 1:1, respectively.

According to at least one optional embodiment, the first acidic monomer comprises about 0.6% to about 10% of the dental adhesive system by weight. Further optionally, the second acidic monomer comprises about 2% to about 20% of the dental adhesive system by weight. In at least one optional embodiment, the comonomer comprises about 2% to about 40% of the dental adhesive system by weight.

According to at least one optional embodiment, the at least one comonomer comprises two comonomers selected from the group consisting of 2-hydroxyethyl methacrylate, bisphenol A diglycidyl methacrylate, triethylene glycol dimethacrylate, 1,6-hexanediol dimethacrylate, ethoxylated bisphenol A diglycidyl methacrylate, and urethane dimethacrylate. Further optionally, the initiator comprises about 0.05% to about 2% of the dental adhesive system by weight. In yet at least one other optional embodiment, the initiator comprises at least one photosensitive ketone and at least one tertiary amine, and optionally comprises at least one solvent.

According to certain embodiments, the dental adhesive system displays an initial bond strength to zirconia that is greater than 10 MPa as measured with the #5 gel cap method when polymerized. Further optionally, the adhesive system displays an initial bond strength to zirconia that is at least about 14 MPa as measured with the #5 gel cap method when polymerized.

The present application further relates to a method of bonding zirconia to a surface, comprising providing a first acidic monomer having an ethylenically unsaturated polymerizable group of the general formula $CH_2=CX-C(O)-R$ wherein X is hydrogen, methyl or a lower alkyl group, and wherein R is a phosphoric acid group or phosphonic acid group; providing a second acidic monomer having an ethylenically unsaturated polymerizable group of the general formula $CH_2=C_X-C(O)-R_1$ wherein X is hydrogen, methyl or a lower alkyl group, and wherein $R_1$ comprises a carboxylic acid group; providing at least one comonomer selected from the group consisting of 2-hydroxyethyl methacrylate, bisphenol A diglycidyl methacrylate, triethylene glycol dimethacrylate, 1,6-hexanediol dimethacrylate, ethoxylated bisphenol A diglycidyl methacrylate, and urethane dimethacrylate; providing an initiator comprising at least one photosensitive ketone and at least one tertiary amine; combining all provided materials and applying those materials to a zirconia dental appliance; and polymerizing the combined materials applied to the zirconia dental appliance such that the initial bond between the polymerized materials and the zirconia is at least about 10 MPa as measured with the #5 gel cap method.

According to at least one optional embodiment, the method utilizes the provided materials in the following percentages: the first acidic monomer comprises about 1% to about 5% of the provided materials by weight; the second acidic monomer comprises about 2% to about 10% of the of the provided materials by weight; the comonomer comprises about 4% to about 36% of the provided materials by weight; the initiator comprises about 0.05% to about 3% of the dental adhesive system by weight; and a solvent comprises about 40% to about 90% of the provided materials by weight.

In yet at least one additional optional embodiment, wherein none of the provided monomers comprise a halogen group. Further optionally, the initial bond between the polymerized materials and the zirconia is at least about 14 MPa as measured with the #5 gel cap method. As an additional option, the provided materials are polymerized via light curing. Finally, as an additional option, the bond between the polymerized materials and the zirconia is at least about 10 MPa as measured with the #5 gel cap method when exposed to water at 100° C. for 72 hours.

DESCRIPTION

A. Zirconia Dental Adhesive System

According to at least one embodiment herein, a dental adhesive or primer system is provided for creating or enhancing a strong and lasting bond between dental resins, etched and unetched dentin, cements, composites and other dental materials to zirconia ceramics as well as other dental substrates, such as dentin, metal, and other ceramics. In at least one embodiment, a dental adhesive system comprises a first monomer and a second monomer, wherein each monomer is acidic.

Further, according to at least one embodiment, a dental adhesive system comprises a first polymerizable acidic monomer and a second polymerizable acidic monomer, wherein the first polymerizable acidic monomer comprises an ethylenically unsaturated polymerizable group or moiety of the general formula $CH_2=C_X-C(O)-$ wherein X is hydrogen, methyl or a lower alkyl group, and the first polymerizable monomer further comprises a phosphoric or phosphonic acid group of general formula $-OP(O)(OH)_2$, $-OP(O)(OH)$, $-C-P(O)(OH)_2$ and $-C-P(O)(OH)$. For exemplary purposes, the phosphoric or phosphonic acid group is methacryloyloxyalkyl dihydrogenphosphates $CH_2=C(CH3)COO(CH_2)_nOP(O)(OH)_2$ or $CH_2=C(CH3)COO(CH_2)_nP(O)(OH)_2$ wherein n is an integer from 2 to 20. Additionally, according to at least one exemplary embodiment, the second polymerizable acidic monomer comprises an ethylenically unsaturated polymerizable group or moiety of the general formula $CH_2=C_X-C(O)-$ wherein X is hydrogen, methyl or a lower alkyl group, and wherein the second polymerizable acidic monomer further comprises a carboxylic acid group of the general formula $-C(O)OH$. For exemplary purposes, the carboxylic acidic group may be tetrahydrofurfuryl cyclohexene dimethacrylate ("TCDM", the reaction product of Epiclon B-4400 with HEMA, available from Dainippon Inc. and Chemicals Inc., Ft. Lee, N.J.); the reaction product of 3,3'4,4'-diphenylsulfone tetracarboxylic dianhydride and 2-HEMA (hereinafter "DSDM") or biphenyl dimethacrylate (hereinafter "BPDM", the reaction product of an aromatic dianhydride with an excess of 2-HEMA as described in U.S. Pat. No. 5,348,988). For convenience, the structures of each of these exemplary carboxylic acid groups are set forth below:

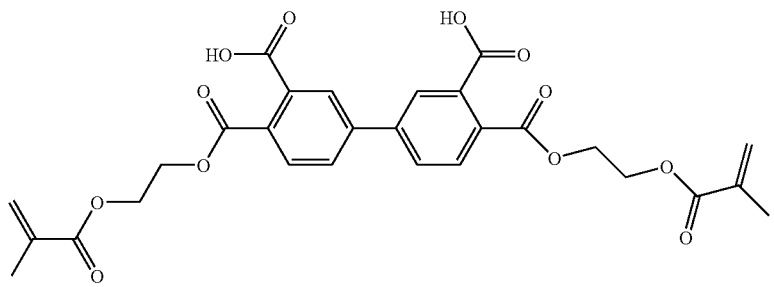

BPDM

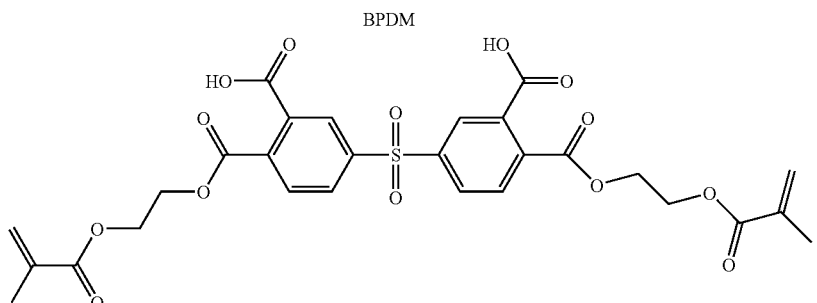

DSDM

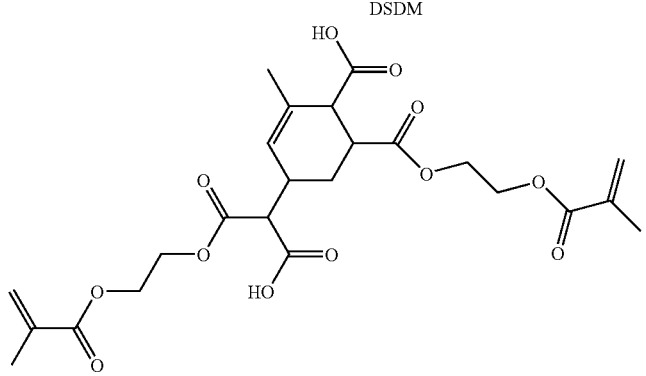

TCDM

According to at least one embodiment of the present application, a dental adhesive system for bonding zirconia materials may further comprise an additional monomer or monomers, hereinafter referred to as "comonomers", which may include monomethacrylates such as 2-hydroxyethyl methacrylate (HEMA) and dimethacrylates such as bisphenol A diglycidyl methacrylate (BisGMA), triethylene glycol dimethacrylate (TEGDMA), 1,6-hexanediol dimethacrylate (HDDMA), ethoxylated bisphenol A diglycidyl methacrylate (BisEMA), urethane dimethacrylate (UDMA). Further, according to at least one embodiment, a dental adhesive system may comprise one or more solvents, including water, ethanol, acetone, or other solvents utilized with dental monomers, or mixtures thereof. According to at least one embodiment, a dental adhesive system further comprises an initiator operable to promote polymerization of the adhesive system. According to at least one exemplary embodiment, the initiator is a photoinitiator operable to initiate polymerization of the dental adhesive system when exposed to a selected wavelength (such as ultraviolet or portions of the visible spectrum of light). Additionally, according to at least one embodiment, a dental adhesive system further comprises one or more silane coupling agents, such as 3-methacryloxypropyl tris(trimethylsiloxy)silane ("MPTS").

In the event that a photoinitiated dental adhesive system is desired, according to at least one embodiment, the initiator may comprise one or more photosensitive ketones and may optionally include a tertiary amine. Typical photosensitive ketones include benzophenone, acetophenone, thioxanthen-9-one, 9-fluorenone, anthraquinone, 4'-methoxyacetophenone, diethoxyacetophenone, biacetyl 2,3-pentadione, benzyl 4,4'-methoxybenzil, 4,4'-oxidibenzil, and camphroquinone (CQ). Typical tertiary amines include ethyl-4-dimethyl amino benzoate, ethyl-2-dimethyl amino benzoate ("EDMAB"), 4,4-bis(dimethylamino)benzophenone, n-methyldiethanolamine, and dimethylaminobenzaldehyde. According to one exemplary embodiment, a combination of CQ and EDMAB is utilized as an initiator. According to at least one exemplary embodiment, an initiator may comprise a photosensitive ketone in the dental adhesive system in a concentration of about 0.05 wt. % to about 1 wt. %, and a tertiary amine with the concentration comprising about 0.2 wt. % to 3 wt. % of the dental adhesive system. According to yet another exemplary embodiment, an initiator may comprise a photosensitive ketone in the dental adhesive system in a concentration of about 0.2 wt. % to 0.4 wt. %, and a tertiary amine with the concentration comprising about 0.6 wt. % to 1.5 wt. % of the dental adhesive system.

Further, according to at least one embodiment of the present application a dental adhesive system may be provided wherein a first part comprising an acidic monomer or monomers may be provided in a separate container from a second part comprising other comonomers and initiator systems, or wherein both the first part and the second part are supplied in a single container. In the event that the first part and the second part are supplied in separate containers, it will be appreciated that the first part and second part may be admixed in predetermined proportions prior to application to the substrates, such as zirconia or a prepared tooth surface.

According to certain exemplary embodiments, a zirconia dental adhesive system comprises: a first acidic acid monomer having a phosphoric or phosphonic acid group, a second acidic acid monomer having a carboxylic acid group, a solvent, a comonomer, and an initiator, wherein: (1) the first acidic acid monomer comprises about 0.5 wt. %, to about 30 wt. %, about 1 wt. % to about 20 wt. %, about 1.2 wt. % to about 10 wt. %, or about 1.4 wt. % to about 3 wt. %, of the dental adhesive system; (2) the second acidic acid monomer having a carboxylic acid group comprising about 2 wt. % to about 30 wt. %, about 3 wt. % to about 20 wt. %, about 4 wt. % to about 15 wt. %; about 4 wt. % to about 10 wt. %, or about 3 wt. % to about 8 wt. %; (3) the comonomer comprises about 0 wt. % to about 40 wt. %, about 10 wt. % to about 30 wt. %, or about 20 wt. % to about 30 wt. %; and (4) the solvent comprises about 30 wt. % to about 97 wt. %, about 60 wt. % to about 91 wt. %, or about 55 wt. % to about 80 wt. %; and (5) the initiator comprises about 0 wt. % to about 3 wt. %, about 0.05 wt. % to about 2 wt. %, or about 0.05 wt. % to about 1.5 wt. %.

In selecting the combination of first acidic monomer, second acidic monomer, and any comonomer, solvent, initiator, and/or silane coupling agent comprising a dental adhesive system, one of ordinary skill in the art will appreciate that properties such as stability of the adhesive system at room temperature, high initial bond strengths (about 10 to 20 MPa or higher with #5 gel-cap shear bond test method, and about 40 MPa when utilizing the Ultradent shear bond test method) may be considerations in selecting the individual elements and their concentrations in the resulting dental adhesive system. Further, those of ordinary skill in the art will appreciate that variants of the above combinations may be employed to produce a polymerizable dental adhesive system or primer system operable to provide a strong bond between zirconia dental materials and dentin, dental resins, cements, metals, and/or other materials.

B. Application of Zirconia Dental Adhesive System

It will be appreciated that a dental adhesive system as described herein may be utilized to bond dental zirconia ceramic restorations with other dental substrates such as metal, dentin, and ceramics. For example, a dental adhesive system as described herein may be applied as a layer to coat to a surface of a zirconia ceramic restoration component, with the zirconia dental adhesive system optionally being allowed to polymerize. Optionally, the polymerization may be initiated through light, heat, free radical initiation, or other methods known in the art.

Thereafter, a cement, composite, or other dental restorative resin, luting composite, or other component is applied over the polymerized or unpolymerized zirconia dental adhesive composition, thereby providing improved strength between the zirconia dental restoration and the cement, composite, or other dental restorative resin, luting composite, or other component. Thereafter, the zirconia restoration may be adhered to a prepared surface such as prepared dentin or enamel, metal, composite or other dental resin or other restorative materials by copolymerizing the zirconia dental adhesive system and the cement, composite, or other dental restorative resin, luting composite, or other component.

It will be appreciated that by applying the layer of zirconia dental adhesive system over the zirconia surface, the zirconia restoration may then be bonded to other dental substrates such as metal, dentin, ceramics with improved strength in the bond such that zirconia restorations may be applied in clinical applications where they would have previously failed. Further, in certain applications, the zirconia dental adhesive system may be used to bond a zirconia restoration directly to dentin, enamel, metal, or other surfaces with a strong bond. Additionally, in all applications, the zirconia surface may optionally be left unprepared, polished, or sandblasted prior to applying the zirconia dental adhesive system over the zirconia surface. It will be appreciated by those skilled in the art that the dental compositions and the methods of the present invention have significant utility in various restorative applications. In determining the efficacy and clinical applicability of the zirconia dental adhesive systems, a series of tests were performed utilizing different embodiments of the zirconia dental adhesive system described herein. As set forth below, the standard shear bond strength method and Ultradent shear bond strength method of testing strength were utilized to compare varying formulas of zirconia dental adhesive systems as described herein.

C. Exemplary Embodiments

The compositions set forth in the following tables are a subset of those prepared according to certain embodiments of the present application, and each was evaluated using the standard shear bond strength method and Ultradent shear bond strength method as summarized below. To ensure consistency, each of the substrates were prepared as followed, and each exemplary embodiment was tested according to the following protocol.

1. Preparation of Substrates

In preparation of testing the zirconia dental adhesive systems set forth below, all substrates were treated as follows:

a. Zirconia Ceramics, Metals, and other Dental Ceramics

Zirconia, metals, other metal oxide ceramics, and other dental ceramics were abraded with wet 600 or 320 grit silicon carbide ("SiC") paper and lightly sandblasted (or as indicated) with aluminum oxide (50 μm) to create clean surface for bonding. The prepared substrate surface was washed by a typical 3-way dental syringe and air-dried.

b. Dentin Substrates

Extracted human teeth were embedded in resin discs, abraded on the facial surface with a model trimmer, and subsequently abraded with wet 600 or 320 grit SiC paper to create a flat and smooth dentin substrate for bonding. Those prepared dentin surfaces noted as being etched were etched by Uni-Etch® brand etchant (available from Bisco, Inc., Schaumburg, Ill.) and rinsed, and those not noted as etched surfaces were simply rinsed and blotted dry. The dentin surface was blot dried with a sponge pellet to remove visible moisture 2. Bond Strength Testing a. Standard Shear Bond Strength Test Procedure ("SSBS"; #5 Gel Cap Method).

In establishing standard shear bond strength ("SSBS") of the following exemplary embodiments of the zirconia dental adhesive system, one or two coats of the exemplary formulation of the zirconia adhesive system indicated were applied to the prepared substrate's surface by a micro-brush. The amount of zirconia adhesive system applied was sufficient to cover the surface of the substrate. Thereafter, the applied zirconia adhesive system was then air dried, and light cured ("LC") for 20 second at 500 mW/cm². A #5 gel cap (bonding area 0.1684 cm²) was filled with a dental cement, in this case, Choice 2™ cement was utilized (available from Bisco Inc.) unless otherwise indicated. Thereafter, the cement or composite was placed on the prepared substrate surface. Any excess cement was removed with a micro-brush and light cured from 2 sides for 40 s (for LC specimens) or as indicated for self-cure (left for 10 min @ 37° C. oven). The samples were stored in deionized (DI) water at 37° C. for the indicated amount of time before being broken using Instron (Model 4466) with crosshead speed of 5 mm/min. Shear bond strength (SBS) was calculated in MPa by dividing the peak load by bonding area. The mean and standard deviations were calculated for several replications (n is as indicated) for each test.

b. Ultradent Method-Shear Bond Strength Test Procedure ("USBS")

In establishing Ultradent shear bond strength ("USBS") of the following exemplary embodiments of the zirconia dental adhesive system, one or two coats of the zirconia dental adhesive composition were applied to the prepared substrate's surface by a micro-brush in an amount sufficient to cover the surface. Thereafter, the applied zirconia adhesive system was then air dried, and light cured ("LC") for 20 second at 500 mW/cm². The indicated cement or composite was thereafter applied to the coated substrate, and the sample was cured according to the manufacturer's instructions. Thereafter, the sample was tested according to the use of the Ultradent shear bond test by using an Ultradent jig as described generally in the article: Pashley et al., Dent. Mater. 11: 117-125 (1995). Each sample was stored in 37° C. water for the indicated amount of time before being broken using Instron (Model 4466) with crosshead speed of 1 mm/min. Shear bond strength (SBS) was calculated in MPa by dividing the peak load by bonding area. Based on the diameter, 2.3798 mm, 1 lb. equals 1 MPa. The mean and standard deviations were calculated for several replications (n is indicated in each table) for each test, with the results set forth below.

EXAMPLES

I. Zirconia Adhesive Composition on Zirconia Surface

According to at least one exemplary embodiment a zirconia dental adhesive system was prepared utilizing the components and concentrations as set forth in Table 1. As will be seen, for the following exemplary embodiments, absolute ethyl alcohol ("EtOH") was used as the solvent unless otherwise noted; 10-methacryloyloxydecyl dihydrogenphosphates $CH_2=C(CH_3)COO(CH_2)_{10}OP(O)(OH)_2$ ("MDP") was used as a first acidic acid monomer, DSDM was used as a second acidic acid monomer, the specified methacrylates of BisGMA and HEMA were provided as comonomers as provided in Table 1, with the resultant standard shear bond strength results listed. Each noted zirconia adhesive system was mixed in a closed container by shaking the components until all monomers dissolved (approximately four to eight hours). In each of the shear bond strength tests performed in Table 1, Choice 2™ cement was utilized (available from Bisco Inc.) as the cement.

TABLE 1

SBS on Zirconia using Zirconia Adhesive Systems (SSBS, in MPa)

| MDP wt. % | DSDM wt. % | EtOH wt. % | Methacrylate wt. % | Initiator wt. % | SSBS in MPa (SD) (#5 gel-cap) |
|---|---|---|---|---|---|
| 1 | 10 | 57.75 | BisGMA 20, HEMA 10 | CQ 0.25, EDMAB 1 | 16.47 (0.89), 2 hrs in water, n = 8 |
| 3 | 10 | 55.75 | BisGMA 20, HEMA 10 | CQ 0.25, EDMAB 1 | 16.63 (2.48), 24 hrs in water, n = 14 |
| 3 | 10 | 55.75 | BisGMA 20, HEMA 10 | CQ 0.25, EDMAB 1 | 15.69 (2.05), 2 hrs in water, n = 10 |
| 6 | 10 | 53.75 | BisGMA 19, HEMA 10 | CQ 0.25, EDMAB 1 | 13.97 (2.89), 24 hrs in water, n = 8 |
| 10 | 10 | 53.75 | BisGMA 15, HEMA 10 | CQ 0.25, EDMAB 1 | 14.85 (2.40), 2 hrs in water, n = 9 |
| 30 | 10 | 28 | BisGMA 20, HEMA 10 | CQ 0.4, EDMAB 1.6 | 9.42 (1.19), 2 hrs in water, n = 8 |
| 3 | 3 | 73 | BisGMA 20, HEMA 10 | CQ 0.25, EDMAB 1 | 15.59 (1.71), 2 hrs in water, n = 8 |
| 3 | 58 | 6 | BisGMA 20, HEMA 10 | CQ 0.54, EDMAB 2.2 | 14.99 (2.03), 2 hrs in water, n = 8 |
| 3 | 80 | 6 | HEMA 8 | CQ 0.54, EDMAB 2.2 | 12.65 (1.51), 2 hrs in water, n = 8 |
| 6.3 | 20.4 | 10 | BisGMA 40.5, HEMA 20.4 | CQ 0.6, EDMAB 1.8 | 17.15 (2.77), 2 hrs in water, n = 10, |
| 3 | 10 | 61 | BisGMA 20, HEMA 5 | CQ 0.25, EDMAB 1 | 16.27 (2.33), 2 hrs in water, n = 8 |
| 0.6 | 2 | 91 | BisGMA 4, HEMA 2 | CQ 0.05, EDMAB 0.2 | 11.12 (0.6), 2 hrs in water, n = 6 |
| 6.3 | 20.4 | 10 | BisGMA 40.5, HEMA 20.4 | CQ 0.6, EDMAB 1.8 | 17.15 (2.77), 2 hrs in water, n = 10 |
| 1.4 | 4.5 | 80 | BisGMA 9, HEMA 4.52 | CQ 0.11, EDMAB 0.45 | 14.88 (1.60), 2 hrs in water, n = 8 |
| 3 | 10 | Acetone 55.75 | BisGMA 20, HEMA 10 | CQ 0.25, EDMAB 1 | 17.06 (2.20), 2 hrs in water, n = 8 |
| 3 | 10 | EtOH 44, water 11 | BisGMA 20, HEMA 10 | CQ 0.25, EDMAB 1 | 16.20 (2.04) 2 hrs in water, n = 8 |

TABLE 1-continued

| | | | | | |
|---|---|---|---|---|---|
| | SBS on Zirconia using Zirconia Adhesive Systems (SSBS, in MPa) |

| MDP wt. % | DSDM wt. % | EtOH wt. % | Methacrylate wt. % | Initiator wt. % | SSBS in MPa (SD) (#5 gel-cap) |
|---|---|---|---|---|---|
| 1.4 | 4.5 (BPDM, no DSDM) | 80 | BisGMA 9, HEMA 4.5 | CQ 0.11, EDMAB 0.45 | 15.12 (3.97), 2 hrs, n = 5 |

II. Zirconia Adhesive Compositions Utilizing Various Comonomers

According to at least one exemplary embodiment a zirconia dental adhesive system was prepared utilizing the components and concentrations as set forth in Table 2. Similar to those exemplary embodiments set forth in Table 1, for the following exemplary embodiments, absolute ethyl alcohol ("EtOH") was used as the solvent unless otherwise noted; 10-methacryloyloxydecyl dihydrogenphosphates $CH_2=C(CH_3)COO(CH_2)_{10}OP(O)(OH)_2$ ("MDP") was used as a first acidic acid monomer, DSDM was used as a second acidic acid monomer. However, the comonomers were varied as noted in Table 2 as provided, with the resultant standard shear bond strength results listed. Each noted zirconia adhesive system was mixed in a closed container by shaking the components until all monomers dissolved (approximately four to eight hours). In each of the shear bond strength tests performed in Table 2, Choice 2™ cement was utilized (available from Bisco Inc.) as the cement.

contrary, those zirconia adhesive systems utilizing less than 20% monomers, including those utilizing less than 10-15% acidic monomers show high initial strength and maintain long term strength within clinically acceptable ranges, for example, displaying long term SSBS of about 10 MPa or better when measured with the #5 gel cap method after 72 hours in 100° water.

III. Zirconia Adhesive Compositions Compared

In one exemplary embodiment, a zirconia dental adhesive system was prepared utilizing 55.75% by wt. ethanol, 3% by wt. MDP, 10% by wt. DSDM, 20% by wt. BisGMA, 10% by wt. HEMA, 0.25% by wt. CQ, and 1% by wt. EDMAB, and the shear bond strength of zirconia materials treated with the zirconia dental adhesive system to various cements was tested against commercially available products marketed as improving the bonding strength to zirconia materials. In particular, the commercially available adhesive or primer system for zirconia was applied to the zirconia surface, and was allowed

TABLE 2

SBS on Zirconia using Zirconia Adhesive (SSBS, in MPa, #5 gel-cap method)

| MDP wt. % | DSDM wt. % | EtOH wt. % | Methacrylate wt. % | Initiator wt. % | SSBS in MPa (SD) (stored in water for 24 hrs or 2 hrs) |
|---|---|---|---|---|---|
| 3 | 3 | 56 | BisGMA 22, TEGDMA 14 | CQ 0.2, EDMAB 0.6 | 9.60 (2.16), 24 hrs, n = 6 |
| 3 | 10 | 52 | BisGMA 21, TEGDMA 13 | CQ 0.2, EDMAB 0.6 | 12.01 (3.44), 24 hrs, n = 8 |
| 3 | 15 | 50 | BisGMA 20, TEGDMA 12 | CQ 0.2, EDMAB 0.5 | 11.87 (1.91), 24 hrs, n = 8 |
| 5 | 3 | 61 | BisGMA 20, TEGDMA 10 | CQ 0.25 EDMAB 1 | 12.93 (1.64), 2 hrs, n = 7 |
| 10 | 10 | 54 | BisGMA 15, TEGDMA 10 | CQ 0.25, EDMAB 1 | 13.85 (3.04), 24 hrs, n = 8 |
| 3 | 10 | 66 | BisGMA 20 | CQ 0.25, EDMAB 1 | 16.56 (1.57), 2 hrs, n = 8 |
| 3 | 10 | 87 | / | / | 12.53 (1.19), 2 hrs, n = 4 |
| 3 | 10 | 53 | BisGMA 20, HEMA 10, MPTS 3 | CQ 0.25, EDMAB 1 | 13.53 (2.53), 24 hrs, n = 8 |
| 3 | 10 | 55 | BisGMA 20, HEMA 10, MPTS 1 | CQ 0.25, EDMAB 1 | 16.38 (2.47), 24 hrs, n = 11 |
| 5 | 10 | 54 | BisGMA 20, HEMA 10, MPTS 1 | CQ 0.25, EDMAB 1 | 14.96 (3.57), 24 hrs, n = 8 |

It will be appreciated that initial bond strengths as shown are high throughout a range of examples, including those examples having a high percentage of the first and second acidic monomers. However, accelerated aging tests of the zirconia adhesive systems at high temperature indicate that those systems with a high percentage of the first and second acidic monomers form a high build surface on the zirconia surface and may weaken significantly over time when exposed to high temperatures in the presence of water. On the to cure per the directions. Those adhesive or primer systems include: Clearfil Ceramic Primer (available from Kuraray); Metal/Zirconia Primer (available from Ivoclar Vivadent); and the composition discussed above, and referred to below as "Zirconia Adhesive A." The cements listed in Table 3 below were then utilized to bond the primed zirconia surface and tested as discussed above. Those results are listed in Table 3 below. It will be appreciated that the SBS displayed when utilizing Adhesive A were significantly higher than any other commercially available product, with the highest test results often resulting in two to three times the shear bond strength of other commercially available zirconia primers or adhesives.

TABLE 3

SBS on Zirconia by using a Zirconia Adhesive composition as described above and commercial zirconia bonding products

| Primer or Adhesive | Cement | SSBS in MPa (SD) |
|---|---|---|
| Clearfil Ceramic Primer (Kuraray) | Panavia F2.0 (Kuraray) | 7.18 (0.83), 2 hrs, n = 8 |
| Clearfil Ceramic Primer (Kuraray) | Panavia F2.0 (Kuraray) | 7.48 (0.89), 24 hrs, n = 10 |
| Clearfil Ceramic Primer (Kuraray) | Duolink (Bisco) | 9.34 (1.91), 24 hrs, n = 9 |
| Clearfil Ceramic Primer (Kuraray) | Choice 2 (Bisco) | 8.16 (2.78), 24 hrs, n = 9 |
| Metal/Zirconia Primer (Ivoclar Vivadent) | Choice 2 (Bisco) | 5.71 (3.22), 24 hrs, n = 10 |
| Metal/Zirconia Primer (Ivoclar Vivadent) | Duolink (Bisco) | 3.84 (2.57), 24 hrs, n = 9 |
| Metal/Zirconia Primer (Ivoclar Vivadent) | MultilinkAutomix (Ivoclar Vivadent) | 5.19 (1.88), 2 hrs, n = 8 |
| Metal/Zirconia Primer (Ivoclar Vivadent) | MultilinkAutomix (Ivoclar Vivadent) | 2.73 (2.36), 24 hrs, n = 10 |
| Zirconia Adhesive A | Panavia F2.0 (Kuraray) | 17.22 (1.98), 24 hrs, n = 9 |
| Zirconia Adhesive A | MultilinkAutomix (Ivoclar Vivadent) | 15.56 (3.58), 24 hrs, n = 9 |
| Zirconia Adhesive A | Duolink (Bisco) | 14.97 (1.47), 2 hrs, n = 9 |
| Zirconia Adhesive A | Duolink (Bisco) | 16.52 (1.17), 24 hrs, n = 10 |
| Zirconia Adhesive A | Choice 2 (Bisco) | 15.69 (2.05), 2 hrs, n = 10 |
| Zirconia Adhesive A | Choice 2 (Bisco) | 16.63 (2.48), 24 hrs, n-14 |

IV. Zirconia Adhesive Composition Shear Bond Strength When Used on Substrates other than Zirconia In one exemplary embodiment, a zirconia dental adhesive system was prepared utilizing 55.75% by wt. ethanol, 3% by wt. MDP, 10% by wt. DSDM, 20% by wt. BisGMA, 10% by wt. HEMA, 0.25% by wt. CQ, and 1% by wt. EDMAB, and the shear bond strength of the zirconia dental adhesive system was tested for various substrates other than zirconia, indicating the increased bonding strength shown when the dental adhesive system is used as described in Example II above. In each of the shear bond strength tests performed in Table 4, Choice 2™ cement was utilized (available from Bisco Inc.) as the cement. These shear bond strengths were compared to bonding tests where only the Choice 2™ cement was utilized. It will be appreciated from the results of Table 4 that use of the zirconia dental adhesive system on the substrate prior to application of the cement improved shear bond strength for all substrates.

TABLE 4

SBS on various dental substrates by using above-described Zirconia Adhesive composition

| Substrate | SSBS in MPa (SD), #5-gel cap Above Described Zirconia Adhesive | SSBS in MPa (SD), #5-gel cap No Adhesive |
|---|---|---|
| Zirconia | 15.69 (2.05), n = 10 | 1.46 (0.29), n = 2 |
| Titanium | 15.07 (2.46), n = 8 | 7.32 (1.12), n = 8 |
| Stainless steel | 15.15 (2.74), n = 9 | 7.19 (0.65), n = 6 |
| gold | 8.71 (1.67), n = 9 | 5.54 (2.21), n = 7 |
| RexIII | 15.07 (2.14), n = 10 | 6.14 (0.44), n = 8 |
| Dentin - unetched | 14.81 (2.50), n = 10, | |
| Dentin - etched | 23.47 (5.09), n = 9 | |

Although the invention has been described in detail with reference to preferred embodiments, variations and modifications exist within the scope and spirit of the invention as described and defined in the following claims.

What is claimed is:

1. A dental adhesive system comprising:
   a zirconia-based ceramic; and
   an adhesive composition applied to the surface of the zirconia-based ceramic, comprising:
   (a) a first acidic monomer having an ethylenically unsaturated polymerizable group of the general formula $CH_2=CX-C(O)-R$ wherein X is hydrogen, methyl or a lower alkyl group, and wherein R comprises a phosphoric acid group or phosphonic acid group having the general formula $-OP(O)(OH)_2$, $-OP(O)(OH)$, $-C-P(O)(OH)_2$ or $-C-P(O)(OH)$;
   (b) a second acidic monomer having an ethylenically unsaturated polymerizable group of the general formula $CH_2=CX-C(O)-R_1$ wherein X is hydrogen, methyl or a lower alkyl group, and wherein $R_1$ comprises a carboxylic acid group having the general formula $-C(O)OH$;
   (c) wherein the first acidic monomer comprises about 1% to about 5% of the dental adhesive system by weight; and
   (d) wherein the second acidic monomer comprises about 2% to about 10% of the dental adhesive system by weight.

2. The dental adhesive system of claim 1, wherein the first acidic monomer is selected from the group consisting of $CH_2=C(CH3)COO(CH_2)_nOP(O)(OH)_2$ and $CH_2=C(CH3)COO(CH_2)_nP(O)(OH)_2$, wherein n is an integer from 2 to 20.

3. The dental adhesive system of claim 1, wherein the second acidic monomer is selected from the group consisting of tetrahydrofurfuryl cyclohexene dimethacrylate, the reaction product of 3,3'4,4'-diphenylsulfone tetracarboxylic dianhydride and 2-hydroxyethyl methacrylate, and biphenyl dimethacrylate.

4. The dental adhesive system of claim 1, further comprising at least one comonomer selected from the group consisting of 2-hydroxyethyl methacrylate, bisphenol A diglycidyl methacrylate, triethylene glycol dimethacrylate, 1,6-hexanediol dimethacrylate, ethoxylated bisphenol A diglycidyl methacrylate, and urethane dimethacrylate.

5. The dental adhesive system of claim 3, further comprising an initiator.

6. The dental adhesive system of claim 5, wherein the initiator comprises at least one photosensitive ketone and at least one tertiary amine.

7. The dental adhesive system of claim 1, wherein neither of the acidic monomers contain a halogen group.

8. The dental adhesive system of claim 1, wherein the ratio of the first acidic monomer to the second acidic monomer is between about 1:10 and 3:1, respectively.

9. The dental adhesive system of claim 1, wherein the ratio of the first acidic monomer to the second acidic monomer is between about 1:5 and 2:1, respectively.

10. A dental adhesive system comprising:
   a zirconia-based ceramic; and
   an adhesive composition applied to the surface of the zirconia-based ceramic, comprising:
   (a) a first acidic monomer having an ethylenically unsaturated polymerizable group of the general formula $CH_2=CX—C(O)—R$ wherein X is hydrogen, methyl or a lower alkyl group, and wherein R is a phosphoric acid group or phosphonic acid group having the general formula $—OP(O)(OH)_2$, $—OP(O)(OH)$, $—C—P(O)(OH)_2$ or $—C—P(O)(OH)$, the first acidic monomer comprising about 1% to about 5% of the composition by weight;
   (b) a second acidic monomer having an ethylenically unsaturated polymerizable group of the general formula $CH_2=C_X—C(O)—R_1$ wherein X is hydrogen, methyl or a lower alkyl group, and wherein $R_1$ comprises a carboxylic acid group having the general formula $—C(O)OH$, the second acidic monomer comprising about 2% to about 10% of the composition by weight;
   (c) at least one comonomer selected from the group consisting of 2-hydroxyethyl methacrylate, bisphenol A diglycidyl methacrylate, triethylene glycol dimethacrylate, 1,6-hexanediol dimethacrylate, ethoxylated bisphenol A diglycidyl methacrylate, and urethane dimethacrylate;
   (d) an initiator comprising at least one photosensitive ketone and at least one tertiary amine; and
   (e) wherein the ratio of the first acidic monomer to the second acidic monomer is between about 1:10 and 3:1, respectively.

11. The dental adhesive system of claim 10, wherein the comonomer comprises about 2% to about 40% of the dental adhesive system by weight.

12. The dental adhesive system of claim 10, wherein the at least one comonomer comprises two comonomers selected from the group consisting of 2-hydroxyethyl methacrylate, bisphenol A diglycidyl methacrylate, triethylene glycol dimethacrylate, 1,6-hexanediol dimethacrylate, ethoxylated bisphenol A diglycidyl methacrylate, and urethane dimethacrylate.

13. The dental adhesive system of claim 10, wherein the initiator comprises about 0.05% to about 2% of the dental adhesive system by weight.

14. The dental adhesive system of claim 11, further comprising at least one solvent.

15. The dental adhesive system of claim 12, wherein the adhesive system displays an initial bond strength to zirconia that is greater than 10 MPa as measured with the #5 gel cap method when polymerized.

16. The dental adhesive system of claim 12, wherein the adhesive system displays an initial bond strength to zirconia that is at least about 14 MPa as measured with the #5 gel cap method when polymerized.

17. A method of bonding zirconia to a surface, comprising:
   (a) providing a first acidic monomer having an ethylenically unsaturated polymerizable group of the general formula $CH_2=CX—C(O)—R$ wherein X is hydrogen, methyl or a lower alkyl group, and wherein R is a phosphoric acid group or phosphonic acid group having the general formula $—OP(O)(OH)_2$, $—OP(O)(OH)$, $—C—P(O)(OH)_2$ or $—C—P(O)(OH)$, the first acidic monomer comprising about 1% to about 5% of the provided materials by weight;
   (b) providing a second acidic monomer having an ethylenically unsaturated polymerizable group of the general formula $CH_2=C_X—C(O)—R_1$ wherein X is hydrogen, methyl or a lower alkyl group, and wherein $R_1$ comprises a carboxylic acid group having the general formula $—C(O)OH$, the second acidic monomer comprising about 2% to about 10% of the provided materials by weight;
   (c) providing at least one comonomer selected from the group consisting of 2-hydroxyethyl methacrylate, bisphenol A diglycidyl methacrylate, triethylene glycol dimethacrylate, 1,6-hexanediol dimethacrylate, ethoxylated bisphenol A diglycidyl methacrylate, and urethane dimethacrylate;
   (d) providing an initiator comprising at least one photosensitive ketone and at least one tertiary amine;
   (e) combining all provided materials and applying those materials to a zirconia dental appliance; and
   (f) polymerizing the combined materials applied to the zirconia dental appliance such that the initial bond between the polymerized materials and the zirconia is at least about 10 MPa as measured with the #5 gel cap method.

18. The method of claim 17, wherein the comonomer comprises about 4% to about 36% of the provided materials by weight; the initiator comprises about 0.05% to about 3% of the dental adhesive system by weight; and further providing a solvent that comprises about 40% to about 90% of the provided materials by weight.

19. The method of claim 18, wherein none of the provided monomers comprise a halogen group.

20. The method of claim 17, wherein the initial bond between the polymerized materials and the zirconia is at least about 14 MPa as measured with the #5 gel cap method.

21. The method of claim 17, wherein the provided materials are polymerized via light curing.

22. The method of claim 17, wherein the bond between the polymerized materials and the zirconia is at least about 10 MPa as measured with the #5 gel cap method when exposed to water at 100° C. for 72 hours.

23. The dental adhesive system of claim 1, further comprising at least one solvent.

24. A dental restoration comprising:
   a zirconia based restoration having a surface prepared by application of an adhesive comprising,
   (a) a first acidic monomer having an ethylenically unsaturated polymerizable group of the general formula $CH_2=CX—C(O)—R$ wherein X is hydrogen, methyl or a lower alkyl group, and wherein R comprises a phosphoric acid group or phosphonic acid group having the general formula $—OP(O)(OH)_2$, $—OP(O)(OH)$, $—C—P(O)(OH)_2$ or $—C—P(O)(OH)$, the first acidic monomer comprising about 1% to about 5% of the adhesive by weight; and
   (b) a second acidic monomer having an ethylenically unsaturated polymerizable group of the general formula $CH_2=CX—C(O)—R_1$ wherein X is hydrogen, methyl or a lower alkyl group, and wherein $R_1$ comprises a carboxylic acid group having the general formula $—C(O)OH$, the second acidic monomer comprising about 2% to about 10% of the adhesive by weight;
   wherein the prepared surface of the zirconia based restoration is adhered to a tooth.

25. The dental restoration of claim 24, wherein the prepared surface further comprises a dental restorative resin applied over the adhesive, the dental restorative resin selected from the group consisting of: a cement, composite, luting composite or combination thereof.

* * * * *